(12) United States Patent
Kawakami et al.

(10) Patent No.: US 8,183,215 B2
(45) Date of Patent: May 22, 2012

(54) METHOD OF ADMINISTERING ORAL FLORA-IMPROVING AGENT, ANTIBACTERIAL AGENT AND GROWTH PROMOTER

(75) Inventors: Hiroshi Kawakami, Saitama (JP); Nobuhiro Hanada, Tokyo (JP); Susumu Imai, Tokyo (JP)

(73) Assignee: Megmilk Snow Brand Co., Ltd., Sapporo (JP)

( * ) Notice: Subject to any disclaimer, the term of this patent is extended or adjusted under 35 U.S.C. 154(b) by 0 days.

(21) Appl. No.: 12/610,896

(22) Filed: Nov. 2, 2009

(65) Prior Publication Data
US 2010/0048493 A1 Feb. 25, 2010

Related U.S. Application Data

(63) Continuation-in-part of application No. 11/579,600, filed as application No. PCT/JP2005/008348 on May 6, 2005, now abandoned.

(30) Foreign Application Priority Data

May 7, 2004 (JP) ................................ 2004-139080

(51) Int. Cl.
*A01N 43/04* (2006.01)
*A61K 31/70* (2006.01)
*A61K 8/02* (2006.01)

(52) U.S. Cl. ............................. 514/25; 424/49; 424/401
(58) Field of Classification Search ........................ None
See application file for complete search history.

(56) References Cited

U.S. PATENT DOCUMENTS

| | | | |
|---|---|---|---|
| 4,728,641 A | | 3/1988 | Tubaro et al. |
| 4,831,021 A | | 5/1989 | Tubaro et al. |
| 5,066,496 A | * | 11/1991 | Szabo et al. ................. 424/570 |
| 5,386,027 A | * | 1/1995 | Krivan et al. .............. 536/123.1 |
| 5,738,113 A | * | 4/1998 | Connelly ..................... 128/898 |
| 5,831,079 A | | 11/1998 | Hanagata et al. |
| 6,998,392 B2 | * | 2/2006 | Clandinin et al. ............. 514/54 |

FOREIGN PATENT DOCUMENTS

| | | |
|---|---|---|
| CN | 1486194 | 3/2004 |
| DE | 44 30 041 | 2/1996 |
| EP | 0 136 438 | 4/1985 |
| GB | 1269846 | 4/1972 |
| JP | 60-84296 | 5/1985 |
| JP | 11-209756 | 8/1999 |
| JP | 2001-158735 | * 6/2001 |
| WO | WO 02/40051 | 5/2002 |

OTHER PUBLICATIONS

European Patent Office issued an European Search Report dated Mar. 17, 2010, Application No. 05 73 7369.
Schwab U. et al., Binding of *Staphylococcus aureus* to fibronectin and glycolipids on corneal surfaces., German Journal of Ophthalmology, Nov. 1996, 5(6) 417-421.
Hiroshi Kawakami, "Milk Yurai Sialic Acid Ganyu Seibun no Seitai Bogyo Kino—Ikujiyo Chosei Funnyu eno Oyo-", Gekkan Medical Science Digest, vol. 29, No. 13, 2003, pp. 532 to 533.
Lekholm U. et al., Gangliosides in Human Palatal Oral Epithelium., Archives of Oral Biology, 1979, vol. 24, No. 1, pp. 47 to 51.
International Search Report in PCT/JP2005/008348 mailed Sep. 13, 2005.
Chinese Office Action mailed Jan. 5, 2011 in corresponding Chinese Application No. 200580014415.3 with English translation of pertinent portion.

* cited by examiner

*Primary Examiner* — Traviss C McIntosh, III
(74) *Attorney, Agent, or Firm* — Young & Thompson

(57) ABSTRACT

It is intended to provide an oral flora-improving agent capable of forming a favorable flora in the oral cavity and a food or a drink for improving the oral flora. An oral flora-improving agent containing as an active ingredient a ganglioside and a food, a drink, or a feed for improving the oral flora containing the ganglioside exhibit an antibacterial effect on harmful bacteria in the oral cavity, which are undesirable from the viewpoint of decay and diseases such as periodontal disease, and a growth-improving effect on useful bacteria to be preserved in the oral cavity. Further, the ganglioside is efficaciously used as an active ingredient in an antibacterial agent or an antibacterial drink, food, or feed, a growth promoter, or a food, a drink, or a feed for promoting growth.

8 Claims, No Drawings

METHOD OF ADMINISTERING ORAL FLORA-IMPROVING AGENT, ANTIBACTERIAL AGENT AND GROWTH PROMOTER

TECHNICAL FIELD

The present invention relates to an oral flora-improving agent, an antibacterial agent, and a growth promoter each containing as an active ingredient a ganglioside. Also, the present invention relates to a drink and food or feed having an oral flora-improving effect, an antibacterial effect, and a growth promoting effect, and having ganglioside blended therewith.

BACKGROUND ART

It is said that many bacteria live inhuman oral cavities as well as in digestive tracts in the number of species of about 300 to 400 and in the number of individuals of above 6 billions. Those bacteria live in colonies in the oral cavity to form an oral flora. Those vice bacteria in the oral cavity cause bacterial infections such as decay (caries) and periodontal diseases, which are two main diseases in the field of dentistry. Most of the bacteria are present not only in saliva but also plaques that can be said to be clumps of oral bacteria, and adhere to the surfaces of teeth and gaps between the teeth and gingivae. Among the diseases caused by the oral bacteria, attention has been focused mainly on decay (caries) and periodontal diseases. As a result, many studies have been made intensively on components of bacteriostats and bactericides for dental decay bacteria and periodontal disease bacteria. Antibacterial components for preventing decay include bactericides such as chlorhexidine, antibiotics, nonionic (non-ionic) and anionic (negative ionic) surfactants (see, for example, Patent Documents 1 to 4). However, some of the antibacterial components also have side effects such as toxicity. Some of the antibacterial components have disadvantages in that when the antibacterial components are orally taken, the antibacterial components present uncomfortable bitterness or stain the teeth or oral mucous membrane. On the other hand, recently, it has been found to utilize components of materials that are daily taken as food, such as catechin in tea and polyphenol compounds derived from various kinds of plants, as active ingredients. However, there remain problems to be solved in respect of their efficacy. For example, an unattainable amount of such the component is needed if the component is to be obtained from ordinary food. Also, there are many practical problems to be solved. For example, to increase the efficacy, it is necessary to take a specific antibody to dental decay bacteria simultaneously. Further, recently, there is a need to control not only dental decay bacteria but also oral bacteria from the viewpoints of periodontal diseases, halitosis, and oral hygiene, and there are reports on components that inhibit the growth of *Porphyromonas gingivalis* and *Prevotella intermedia* which are representative periodontal disease bacteria (see, for example, Nonpatent Document 1).

The bacteria that constitute the oral flora include both harmful pathogenic bacteria (malignant bacteria) and harmless and useful bacteria (beneficial bacteria). Known harmful bacteria in the oral cavity include *Streptococcus sobrinus, Streptococcusmutans, Streptococcus anginosus, Staphylococcus aureus*, and the like. Known useful bacteria include *Streptococcus mitis*, and the like. *Streptococcus sobrinus*, which is known as a dental decay bacterium, is stronger in harmness than *Streptococcus mutans* and is notorious as a cause of caries in the clinical field. *Streptococcus anginosus* is often detected from the oral cavity of patients suffered from esophageal cancer and hence the possibility is suggested that *Streptococcus anginosus* will be a cause of esophageal cancer. Further, *Staphylococcus aureus* is not only widely known as a pathogen of various abscesses but also is said to cause a complication such as pneumonia accompanying a decrease in immunity or infection with virus such as influenza, which can be a direct cause for gravity of the disease or death. On the other hand, *Streptococcus mitis* is a habitant that generally exists in the oral cavity and is said to occupy 80% of the oral bacteria, and is known to be an important bacterial species for forming a constant flora.

The present invention relates to an oral flora-improving agent containing a ganglioside as an active ingredient and to a drink, a food or a feed for improving the oral flora. Gangliosides are known to prevent infection by antagonistically inhibiting viruses, bacteria, bacterial toxins, and the like from attaching to trachea, or digestive tracts. However, it has not been known up to recently that gangliosides themselves have antibacterial effects. It is yet a novel finding that gangliosides have antibacterial effects against harmful oral bacteria and simultaneously growth promoting effects for useful oral bacteria. The inventors of the present invention have already filed a patent application for an invention on obtaining effects for preventing and improving periodontal diseases by using a compound having a sphingosine skeleton as an active ingredient (see Patent Document 5). The compound having a sphingosine skeleton includes a ganglioside. However, this invention is based on the finding that the compound having a sphingosine skeleton has the effect of inhibiting the bone resorption effect of osteoclasts and is effective in preventing periodontal diseases by suppressing a decrease in alveolar bone. Thus, this invention is different from the present invention that relates to the finding that gangliosides have antibacterial effect and to an oral flora-improving agent that has antibacterial effects to harmful oral bacteria and growth promoting effects for useful oral bacteria that always inhabit, simultaneously.

Recent studies revealed the problem in which the bactericides, antibiotics, and surfactants having the above-mentioned antibacterial components suppress the growth of almost all the bacteria that are present in the oral cavity therefore those bactericides, antibiotics, and surfactants are excellent in bactericidal effects, but those bactericides, antibiotics, and surfactants also break the oral flora to a greater extent. Inhibition of the growth of useful oral bacteria that are generally dominant in the oral flora makes the oral flora unstable, which will possibly lead to proliferation of harmful oral bacteria.

Therefore, instead of using a bactericide having a wide antibacterial spectrum for preventing various bacteria to kill all bacteria in the oral cavity, there is a demand for leaving useful bacteria, which provide effects desirable to living organism by allowing presence in the oral cavity, as they are to be utilized.

Further, there is a demand for an antibacterial agent that has an antibacterial effect against harmful bacteria in the oral cavity but has growth promoting effects without inhibiting the growth thereof, and is mild to useful oral bacteria.

Patent Document 1: JP-A-09-286712
Patent Document 2: JP-A-11-147814
Patent Document 3: JP-A-09-240816
Patent Document 4: JP-A-2001-064163
Patent Document 5: JP-A-2001-158735
Nonpatent Document 1: Ishikawa, Hiroki and four others, Bulletin of Japan Periodontics Society, Vol. 45, No. 1, 105-112, 2003.

DISCLOSURE OF THE INVENTION

Problems to be Solved by the Invention

It is an object of the present invention to provide an oral flora-improving agent and a drink or a food for improving oral flora that do not kill all the bacteria in the oral cavity but that have an antibacterial effect against undesirable bacteria from the viewpoints of diseases such as decay and periodontal diseases and a growth promoting effect for oral bacteria to be preserved thereby forming a desirable flora in the oral cavity. Also, it is another object of the present invention to provide an antibacterial agent or antibacterial drink and food that has an antibacterial effect against undesirable bacteria in the oral cavity. Further, it is another object of the present invention to provide an oral bacteria growth promoter and a drink or a food for promoting an oral bacterium that have a growth promoting effect to oral bacteria to be preserved.

Means for Solving the Problems

The inventors of the present invention have made extensive studies on food components that exhibit an antibacterial effect against undesirable bacteria among bacteria in the oral cavity from the viewpoint of diseases such as decay and periodontal diseases but have a growth promoting effect to bacteria in the oral cavity to be preserved from the viewpoint of forming desirable flora in the oral cavity. As a result, the inventors of the present invention have newly found that gangliosides separated and purified from milk of a mammal have such the effects, thereby achieving the present invention. Gangliosides are known to prevent infection by antagonistically inhibiting viruses, bacteria, bacterial toxins, and the like from attaching to air tubes, i.e., tracheae, or digestive tracts. However, it has not been known up to recently that gangliosides themselves have an antibacterial effect. It is yet a novel finding that gangliosides have an antibacterial effect against harmful oral bacteria and simultaneously growth promoting effects for useful oral bacteria. As described above, for example, *Streptococcus sobrinus, Streptococcus anginosus*, and *Staphylococcus aureus* are known as the harmful oral bacteria. Known useful bacteria include *Streptococcus mitis*, and the like. Investigation on the effect of the gangliosides purified from milk on those bacteria in the oral cavity revealed that all the gangliosides have an antibacterial effect against harmful bacteria and a growth promoting effect to useful bacteria. That is, the present invention relates to an oral flora-improving agent that contains a ganglioside as an active ingredient. Further, the present invention relates to a food, a drink, or a feed for improving the oral flora having blended therein a ganglioside.

Further, the present invention relates to an antibacterial agent and antibacterial drink, food, or feed each of which contains a ganglioside as an active ingredient and has an antibacterial effect against undesirable bacteria in the oral cavity. The antibacterial agent, antibacterial drink, food, or feed of the present invention has an antibacterial effect against harmful oral bacteria but has no antibacterial effect to useful oral bacteria, so such the antibacterial agent and antibacterial drink, food, or feed are very effective.

Further, the present invention relates to a growth promoter and growth promoting drink, food, or feed that contain a ganglioside as an active ingredient and has a growth promoting effect to oral bacteria to be preserved in the oral cavity. The growth promoter and growth promoting drink, food, or feed have a growth promoting effect to useful oral bacteria but have no growth promoting effect to harmful oral bacteria but have an antibacterial effect thereto instead, so such the growth promoter and growth promoting drink, food, or feed are very effective.

EFFECTS OF THE INVENTION

Prevention of the growth of harmful bacteria and promotion of the growth of useful bacteria that always exist by gangliosides are extremely effective for maintaining the oral flora in a good state and can be utilized for the prevention of various diseases caused by the oral bacteria. Therefore, by blending gangliosides to form a preparation, an oral flora-improving agent that contains a ganglioside as an active ingredient and has the effects of preventing the growth of harmful bacteria and promoting the growth of useful bacteria that always exist can be provided. Further, by blending gangliosides in a drink or a food, a drink, a food, or feed for improving the oral flora can be provided.

Further, the present invention can provide an antibacterial agent and an antibacterial drink, food, or feed that contain a ganglioside as an active ingredient and have an antibacterial effect against undesirable bacteria in the oral cavity.

Further, the present invention can provide a growth promoter and a drink, food, or feed for promoting growth that contain a ganglioside as an active ingredient and have a growth promoting effect to oral bacteria to be preserved.

BEST MODE FOR CARRYING OUT THE INVENTION

The origin of the gangliosides according to the present invention is not particularly limited. However, gangliosides obtained from milk as a raw material are desirable as gangliosides to be used as the oral flora-improving agent or the drink, food, or feed for improving the oral flora; the antibacterial agent or the antibacterial drink, food, or feed; and the growth promoter or the drink, food, or feed for growth promotion. The fact that milk contains much ganglioside GD3 is a reason that milk is desirable as a raw material. In a case where gangliosides are prepared from milk or milk is concentrated to increase the content of gangliosides, the method therefor is not particularly limited. For example, gangliosides can be prepared as fat globule membranes from butter milk by a method such as dialysis, ammonium sulfate fractionation, gel filtration, or isoelectric point precipitation. Also, as disclosed in JP-A-63-269992, a material containing a high content of gangliosides can be prepared by preparing a decomposate solution from milk with a proteolytic enzyme and subjecting the decomposate solution to gel filtration or ultrafiltration. Alternatively, gangliosides can be prepared by using a microfiltration membrane having a pore size of 0.1 μm or less or by a process employing an ultrafiltration membrane having a molecular weight cut-off of 100,000 Da or more (JP-A-05-269353). Further, ganglioside GM3 can be prepared by hydrolyzing ganglioside GD3 (JP-A-05-279379) or by reacting sialidase on ganglioside GD3.

According to the present invention, an oral flora-improving agent or an oral flora-improving drink, food, or feed; an antibacterial agent or an antibacterial drink, food, or feed; and a growth promoter or a growth promoting drink, food, or feed can be provided. Further, in the present invention, ganglioside GD3 and ganglioside GM3 do not have to be separated and may be used as mixtures thereof. It is preferable from the viewpoint of saving labor and cost involved in purification to use a high ganglioside content fraction that contains ganglioside GT3 as well as ganglioside GM3 and ganglioside GD3 in the oral flora-improving agent or the oral flora-improving drink, food, or feed; the antibacterial agent or the antibacterial drink, food, or feed; and the growth promoter or the growth promoting drink, food, or feed according to the present invention.

When the oral flora-improving agent, antibacterial agent, and growth promoter are used as medicines, their forms are not particularly limited and depending on the administration method, kind of disease to which they are applied, shape and sites and other conditions, various forms such as tablets, capsules, powder, granules, and drinks can be selected as appropriate. Therefore, the above-mentioned oral flora-improving agent, antibacterial agent, and growth promoter of the present invention can be used as they are as medicines or in combination with various additives (i.e., sugars, starches, and alcohols) which are generally used, such as carriers and diluents.

The oral flora-improving agent, antibacterial agent, and growth promoter of the present invention can be prepared and used in various forms that can be applied to the oral cavity including tooth care preparations such as toothpaste, tooth powder, and tooth liquid, mouth wash, gargles, oral paste, gingival massage cream, gargling tablets, and lozenges.

As the other components that are mixed with the oral flora-improving agent, antibacterial agent, and growth promoter of the present invention, appropriate components can be used depending on the purpose and mode of use. For example, in preparing the tooth powder, polishing agents such as dicalcium phosphate dihydrate, anhydrous dicalcium phosphate, monocalcium phosphate, tricalcium phosphate, calcium carbonate, calcium pyrophosphate, insoluble sodium metaphosphate, amorphous silica, crystalline silica, aluminosilicate, aluminum oxide, aluminum hydroxide, trimagnesium phosphate, magnesium carbonate, magnesium sulfate, titanium oxide, and resin can be blended in amounts of generally 5 to 95%, preferably 15 to 60%. In preparing paste compositions such as toothpaste, binders such as carboxymethylcellulose sodium, methylcellulose, carboxymethylhydroxyethylcellulose sodium, hydroxyethylcellulose, sodium alginate, carrageenan, gum arabic, xanthan gum, tragacanth gum, karaya gum, polyvinyl alcohol, sodium polyacrylate, carboxyvinyl polymer, and polyvinylpyrrolidone can be blended in amounts of generally 0.3 to 5%. In preparing a paste-like or liquid composition such as toothpaste or mouth wash, viscosity improvers such as polyethylene glycol, ethylene glycol, sorbitol, glycerin, propylene glycol, 1,3-butylene glycol, xylit, maltit, and lactit can be blended in amounts of generally 10 to 70%. Further, as necessary, essential oils such as peppermint and spearmint; flavor materials such as 1-menthol, carvone, eugenol, and anethol; sweeteners and antiseptics such as saccharin sodium, stevioside, neohesperidyl dihydrochalcone, glycyrrhizin, perillartin, and p-methoxycinnamic aldehyde are blended as appropriate. Note that in the present invention, active ingredients such as mutanase, sorbic acid, alexidine, hinokitiol, cetylpyridinium chloride, alkylglycine, alkyl diaminoethyl glycinate, allantoin, ε-aminocaproic acid, tranexamic acid, azulene, vitamin E, water-soluble mono- or diphosphate, quaternary ammonium compounds, sodium chloride, and herbal medicine extracts can be blended.

The oral flora-improving, antibacterial, and growth promoting drink or food of the present invention can be prepared and used in various forms that are applied to the oral cavity, such as candies, chewing gums, cold beverages, milk beverages, fermented milk, ice cream and whipped cream.

To blend gangliosides in a drink or a food to prepare the oral flora-improving, antibacterial, and growth promoting drink and food of the present invention, for example, gangliosides can be directly added to main materials of the drink or food or a mixture of gangliosides and water can be added to the drink or food such as candies, chewing gums, cold beverages, milk beverages, fermented milk, cheese food, confectionery, bread and snack food.

The oral flora-improving, antibacterial, and growth promoting feed of the present invention can be prepared and used in a general form of feed that is given to animals such as a pet food. To blend gangliosides in feed to prepare the oral flora-improving, antibacterial and growth promoting feed of the present invention, for example, gangliosides can be directly added to main materials of the feed or a mixture of gangliosides and water can be added to feed such as a pet food.

Intake or dosage of each of the oral flora-improving agent, antibacterial agent, and growth improving agent according to the present invention is not settled in general as depending on the kind of the oral bacteria and the like, in the case of an adult whose weight is 60 Kg, the intake or dosage is generally 0.1 to 100 mg, or preferably 1 to 10 mg per day.

In the present invention, when gangliosides are blended in general food, the amount of the gangliosides with respect to food is usually 0.1 mg to 10 g/100 g, preferably 1 mg to 1 g/100 g. If the amount of gangliosides is less than 0.1 mg/100 g, the effects obtained are weak and the amount of gangliosides of more than 10 g/100 g provides the effects not so much improved.

Note that in the present specification, all percents (%) are by weight unless otherwise stated.

Hereinafter, the present invention is explained in more detail by way of a test example and examples. However, the present invention is not limited thereto.

TEST EXAMPLE 1

Assay of Antibacterial Activity

The influences of gangliosides on oral bacteria were examined by Radial Diffusion Assay. That is, 3 mg of Tryptic Soy medium (Difco), 20 µl of Tween 20, and 100 mg of agarose were dissolved in 10 ml of ultrapure water and sterilized. 100 µl of solution of bacteria having an OD620 of 0.2 ($5 \times 10^7$ cfu/ml) was added to the sterilized medium, and then the resultant mixture was dispensed in Petri dishes and allowed to solidify at room temperature. Each solidified medium was provided with a hole of about 2.5 mm in diameter and 5 µl of each solution of ganglioside GM3 or ganglioside GD3 derived from milk for the evaluation of the antibacterial effect was added to the hole and incubated at 37° C. for 1 hour. Further, a sterilized medium obtained by dissolving 0.6 g of Tryptic Soy medium and 100 mg of agarose in 10 ml of ultrapure water was superposed on the solidified medium and left to solidify at room temperature, and then stationary cultured in an incubator at 37° C. After 18 hours, the diameter of a clear zone formed around the hole formed in the medium was measured. A length obtained by subtracting the diameter (mm) of the hole formed in the medium from the diameter (mm) of a clear zone formed by inhibition of the growth of the bacterium was defined as antibacterial activity. On the other hand, when colonies of the bacterium were formed around the hole in the medium and an opaque zone was observed, it was assumed that growth promotion took place, and a length obtained by subtracting the diameter (mm) of the hole formed in the medium from the diameter (mm) of an opaque zone was defined as growth promotion activity. The bacterial strains subjected to the test include *Streptococcus sobrinus* 6715 strain, *Streptococcus anginosus* ATCC33397 strain, and *Staphylococcus aureus* Cowan I strain as harmful oral bacteria;

*Streptococcus agalactiae* ATCC46448 strain and *Actinomyces naeslundii* JCM8349 strain as habitant oral bacteria; and *Streptococcus mitis* GTC495 strain, *Streptococcus mitis* ATCC6249 strain, and *Streptococcus mitis* ATCC903 strain as useful oral bacteria.

Bacitracin, which is an antibacterial component separated from *Bacillus subtilis*, was used as a positive control and a sample showing an antibacterial activity of 2.0 mm or more was judged to be positive (having an antibacterial activity). As for the growth promoting effect, a sample having a growth promoting activity of 1.0 mm or more was judged to be positive (having a growth promoting activity).

TABLE 1

|  | Bacitracin | GM3 | GD3 |
|---|---|---|---|
| *Streptococcus sobrinus* 6715 | + | + | + |
| *Streptococcus anginosus* ATCC33397 | + | + | + |
| *Staphylococcus aureus* Cowan I | + | + | + |
| *Streptococcus mitis* GTC945 | + | * | * |
| *Streptococcus mitis* ATCC6249 | + | * | * |
| *Streptococcus mitis* ATCC903 | + | * | * |
| *Streptococcus agalactiae* ATCC46448 | + | − | − |
| *Actinomyces naeslundii* JCM8349 | + | − | − |

+: Having an antibacterial activity
−: Having no antibacterial activity
*: Having a growth promoting activity The results obtained are shown in Table 1. The results of the tests indicate that samples to which Bacitracin was added as a positive control showed an antibacterial activity for all the strains tested. On the other hand, all the samples to which a solution of ganglioside GM3 or ganglioside GD3 was added showed an antibacterial activity for *Streptococcus sobrinus* 6715 strain, *Streptococcus anginosus* ATCC33397 strain, and *Staphylococcus aureus* Cowan I strain, which are harmful oral bacteria and showed neither an antibacterial activity nor a growth promoting activity for *Streptococcus agalactiae* ATCC46448 strain and *Actinomyces naeslundii* JCM8349 strain, that is, have no effects thereto. On the contrary, samples to which a solution of ganglioside GD3 or ganglioside GM3 was added had a growth promoting activity on the three strains of *Streptococcus mitis*, which is useful bacterium.

The above-mentioned results indicate that ganglioside GM3 or ganglioside GD3 purified from milk each had an antibacterial effect on harmful bacteria but a growth promoting effect on useful bacteria.

REFERENCE EXAMPLE 1

Preparation of Ganglioside Derived from Milk

According to the conventional method of preparing gangliosides (JP-A-63-269992), a ganglioside derived from milk was prepared. That is, trypsin, which is a proteolytic enzyme, was allowed to act on a milk substance containing a ganglioside at 40° C. for 15 hours to decompose proteins and the obtained protein decomposate solution was dialyzed through a membrane having a molecular weight cut-off of 10,000 to obtain a high ganglioside content fraction. The high ganglioside content fraction was freeze-dried and then dissolved in a chloroform-methanol (1:1) solution. The resultant solution was passed through an anion exchange resin (DEAE-Sephadex: produced by Pharmacia) to have the ganglioside adsorbed thereon. Then, the anion exchange resin was washed with a chloroform-methanol (1:1) solution and then the ganglioside was eluted with a 0.1 M aqueous sodium acetate solution-methanol solution. The eluate was concentrated to dryness under reduced pressure, dialyzed to remove salts, and freeze-dried. Detection of the ganglioside fraction (fraction A) thus obtained by thin layer chromatography (resorcinol method) provided that ganglioside GM3: ganglioside GD3 ganglioside GT3=10:90:1. In the oral flora-improving agent or the oral flora-improving drink, food, or feed; the antibacterial agent or the antibacterial drink, food, or feed; and the growth promoter or the growth promoting drink, food, or feed according to the present invention, ganglioside GD3 and ganglioside GM3 do not have to be separated and can be utilized as a mixture of the both. In this case, the fraction A is used.

Further, the fraction A was fractionated. That is, the fraction A was suspended in a chloroform-methanol (8:8 (v/v)) solution and the suspension was added to a silica gel column (Iatrobead; produced by Iatron Laboratories, Inc) and subjected to gradient elution from 8:2 (v/v) to 2:8 (v/v) of a chloroform-methanol solution to fractionate it into a ganglioside GM3 fraction (fraction B), a ganglioside GD3 fraction (fraction C), and a ganglioside GT3 fraction (fraction D). Detection of each ganglioside fraction by thin layer chromatography indicated that each ganglioside fraction had a purity of 95% or more.

EXAMPLE 1

Production of Oral Flora-Improving Powder

Based on the provision of "Powder" in General Rule for Preparations of Commentary of Japan Pharmacopoeia 13th edition, 1.0 wt % of ganglioside GD3 (ganglioside fraction C in Reference Example 1) derived from milk was uniformly mixed with 59.0 wt % of lactose (Japan Pharmacopoeia) and 40.0 wt % of potato starch (Japan Pharmacopoeia) to produce the oral flora-improving powder of the present invention.

EXAMPLE 2

Production of Antibacterial Powder

By the same formulation and method as those in Example 1, the antibacterial powder of the present invention for undesirable oral bacteria was produced.

EXAMPLE 3

Production of Growth Promoting Powder

By the same formulation and method as those in Example 1, the growth promoting powder of the present invention for desirable oral bacteria was produced.

EXAMPLE 4

Production of Tablets

Materials were blended in the formulation as shown in Table 2 and the resultant mixture was compressed by a compression tablet machine (Y-5010-Q manufactured by Fuji Medical Machine) (condition: 1 to 4 ton) to produce the oral flora-improving tablets of the present invention.

TABLE 2

| Name of raw materials | |
|---|---|
| Hydrous crystalline glucose | 93.0 |
| Calcium | 5.0 |
| Sugar ester | 1.0 |
| Milk-derived ganglioside GM3 (Ganglioside fraction B in Reference Example 1) | 0.5 |
| Flavor | 0.5 |
| | 100.0 |

EXAMPLE 5

Production of Fruit Juice Drink

Materials were mixed in the formulation shown in Table 3, heat-sterilized, and packed in a container to produce the oral flora-improving fruit juice drink of the present invention.

TABLE 3

| Name of raw materials | Weight % |
|---|---|
| Mixed isomerized sugar | 15.0 |
| Orange juice | 10.0 |
| Calcium | 0.5 |
| Citric acid | 0.5 |
| Flavor | 0.2 |
| Milk-derived ganglioside (Ganglioside fraction A in Reference Example 1) | 0.1 |
| Water | 73.7 |
| | 100.0 |

EXAMPLE 6

Production of Processed Cheese

Materials were mixed in the formulation shown in Table 4, emulsified at an emulsifying temperature of 85° C. to produce the oral flora-improving processed cheese of the present invention.

TABLE 4

| Name of raw materials | Weight % |
|---|---|
| Gouda cheese | 43.0 |
| Cheddar cheese | 43.0 |
| Sodium citrate | 2.0 |
| Milk-derived calcium | 1.0 |
| Milk-derived ganglioside (Ganglioside fraction A in Reference Example 1) | 0.5 |
| Water | 10.5 |
| | 100.0 |

EXAMPLE 7

Production of Toothpaste

Materials were mixed in the formulation shown in Table 5 to form a kneaded product, and the resultant was packed in a container to produce the oral flora-improving toothpaste of the present invention.

TABLE 5

| Name of raw materials | Weight % |
|---|---|
| Glycerin | 55.0 |
| Silicon dioxide | 20.0 |
| Dicalcium phosphate dihydrate | 10.0 |
| Milk-derived ganglioside (Ganglioside fraction A in Reference Example 1) | 5.0 |
| Xanthan gum | 1.0 |
| Peppermint flavor | 1.0 |
| Titanium dioxide | 0.7 |
| Sodium fluoride | 0.3 |
| Distilled water | 7.0 |
| | 100.0 |

EXAMPLE 8

Production of Toothpaste

By the same formulation and method as those in Example 7, the antibacterial toothpaste of the present invention for undesirable oral bacteria was produced.

EXAMPLE 9

Production of Toothpaste

By the same formulation and method as those in Example 7, the growth promoting toothpaste of the present invention for desirable oral bacteria was produced.

EXAMPLE 10

Production of Gargle

Materials were blended in the formulation as shown in Table 6, and the oral flora-improving gargle of the present invention was produced.

TABLE 6

| Name of raw materials | Weight % |
|---|---|
| Ethyl alcohol | 8.0 |
| Sorbitol | 5.0 |
| Propylene glycol | 5.0 |
| Milk-derived ganglioside (Ganglioside fraction A in Reference Example 1) | 5.0 |
| Flavor | 1.0 |
| Distilled water | 76.0 |

EXAMPLE 11

Production of Oral Flora-Improving Chewing Gum

Materials were mixed in the formulation shown in Table 7 and molded by a conventional method to produce the oral flora-improving chewing gum of the present invention.

TABLE 7

| Name of raw materials | Weight % |
|---|---|
| Gum base | 20.0 |
| Corn syrup | 10.0 |
| Dextrose monohydrate | 10.0 |
| Lactose | 5.0 |
| Glycerin | 5.0 |

TABLE 7-continued

| Name of raw materials | Weight % |
| --- | --- |
| Milk-derived ganglioside (Ganglioside fraction A in Reference Example 1) | 1.0 |
| Water | 49.0 |
| | 100.0 |

EXAMPLE 12

Production of Antibacterial Chewing Gum

By the same formulation and method as those in Example 11, the antibacterial chewing gum of the present invention for undesirable oral bacteria was produced.

EXAMPLE 13

Production of Growth Promoting Chewing Gum

By the same formulation and method as those in Example 11, the growth promoting chewing gum of the present invention for desirable oral bacteria was produced.

EXAMPLE 14

Production of Oral Flora-Improving Dog Food

Materials were mixed in the formulation shown in Table 8 and sterilized at 120° C. for 4 minutes to produce the oral flora-improving dog food of the present invention.

TABLE 8

| Name of raw materials | Weight % |
| --- | --- |
| Skimmed milk powder | 14.0 |
| Soybean cake | 12.0 |
| Palm oil | 23.2 |
| Soybean oil | 4.0 |
| Corn oil | 2.0 |
| Cellulose | 2.8 |
| Mineral mixture | 2.0 |
| Milk-derived ganglioside (Ganglioside fraction A in Reference Example 1) | 1.0 |
| Water | 39.0 |
| | 100.0 |

Industrial Applicability

The oral flora-improving agent, antibacterial agent, and growth promoter of the present invention can be used as medicines as they are and in addition, the oral flora-improving agent, antibacterial agent, and growth promoter can be combined with various additives generally used, such as carriers and diluents, as necessary.

Further, according to the present invention, gangliosides can be directly added to main materials of a drink or a food or a mixture of ganglioside with water can be added to various forms that can be applied to the oral cavity, such as candies, chewing gums, cold beverages, milk beverages, fermented milk, ice cream, and whipped cream. Accordingly, oral flora-improving, antibacterial, and growth promoting drink and food can be prepared.

Further, gangliosides can be directly added to main materials of feed. Alternatively, a mixture of gangliosides with water can be prepared into forms that can be generally added to animals and can be added to feed such as pet food. Accordingly, an oral flora-improving, antibacterial, and growth promoting feed can be prepared.

The invention claimed is:

1. A method of treating or inhibiting dental carries by improving the oral flora in a subject, the method comprising applying to an oral cavity of a subject in need thereof an effective amount of a composition comprising a ganglioside, wherein the composition is a dentifrice and the effective amount inhibits growth of at least one of *Streptococcus sobrinus, Streptococcus anginosus* and *Staphylococcus aureus* in the oral cavity and promotes growth of beneficial bacteria in the oral cavity.

2. The method of claim 1, wherein the ganglioside is at least one of ganglioside GD3, ganglioside GM3 or a combination thereof.

3. The method of claim 1, wherein the dentifrice is selected from the group consisting of toothpaste, tooth powder, tooth liquid, mouth wash, gargle, oral paste, gingival massage cream, gargling tablet, lozenge and chewing gum.

4. The method of claim 1, wherein the ganglioside is derived from milk.

5. The method of claim 1, wherein the beneficial bacteria is *Streptococcus mitis*.

6. The method of claim 1, wherein the composition is applied to the oral cavity of the subject in an amount of 0.1 to 100 mg/60 kg/day.

7. The method of claim 1, wherein the composition is applied to the oral cavity of the subject in an amount of 1 to 10 mg/60 kg/day.

8. The method of claim 1, wherein the composition is applied to the teeth or gums of the subject.

* * * * *